United States Patent
Murphy et al.

(10) Patent No.: US 6,680,207 B1
(45) Date of Patent: Jan. 20, 2004

(54) DETECTION OF MOLECULES IN SAMPLES

(75) Inventors: Jonathan P. Murphy, East Hagbourne (GB); Anthony Atkinson, Salisbury (GB)

(73) Assignee: Generic Biologicals Limited, Salisbury (GB)

( * ) Notice: Subject to any disclaimer, the term of this patent is extended or adjusted under 35 U.S.C. 154(b) by 0 days.

(21) Appl. No.: 09/554,451

(22) PCT Filed: Nov. 16, 1998

(86) PCT No.: PCT/GB98/03449

§ 371 (c)(1),
(2), (4) Date: May 15, 2000

(87) PCT Pub. No.: WO99/26069

PCT Pub. Date: May 27, 1999

(30) Foreign Application Priority Data

Nov. 14, 1997 (GB) ............................................. 9723955

(51) Int. Cl.$^7$ ...................... G01N 33/566; A01N 37/18; C07K 14/00
(52) U.S. Cl. ........................ 436/501; 514/2; 530/350; 530/399
(58) Field of Search ............................ 435/6, 7.1, 7.2; 436/501, 800; 530/350, 380.1, 399; 514/2

(56) References Cited

U.S. PATENT DOCUMENTS

| | | | | |
|---|---|---|---|---|
| 4,066,405 A | * | 1/1978 | Henkin ..................... 23/230 B |
| 5,506,107 A | * | 4/1996 | Cunningham et al. ..... 435/7.21 |
| 5,534,617 A | | 7/1996 | Cunningham et al. | |

FOREIGN PATENT DOCUMENTS

| WO | WO 90/04788 | 5/1990 |
|---|---|---|
| WO | WO 92/09690 | 6/1992 |
| WO | WO 94/10200 | 5/1994 |

OTHER PUBLICATIONS

Kilhoffer et al., Biochemistry, 1992, vol. 31, pp. 8098–8106.*

Ferrara, P "HGH: Production by genetic engineering for a hormone identical to the natural 22K hormone" *Symposium Quo Vadis?*, Sanofi, May 29–30, Toulouse–Labege, France (1985) 147–155.

Atkinson, T, et al. "Human Growth Hormone: Microbial Expression and purification," *Biotechnology* 1 (1985) 1–6.

Chang, CN, et al., "High–level secretion of human growth hormone by *Escherichia coli*," *Gene* 55 (1987) 189–196.

Gray, G L, et al., "*Pseudomonas Aeruginosa* secretes and correctly processes human growth hormone," *Biotechnology* (1984) 161–165.

Franchi, E, et al., "A new human growth hormone production process using a recombinant *Bacillus subtilis* strain," *J. Biotechnology* 18 (1991) 41–54.

Hsiung, H M, et al., "High–level expression, efficient secretion and folding of human growth hormone in *Escherichia coli,*" *Biotechnology* 4 (1986) 991–995.

Becker, G W et al., "Expression, secretion and folding of human growth hormone in *Escherichia coli,*" *FEBS*, 204:1 (1968) 145–150.

(List continued on next page.)

*Primary Examiner*—Bradley L. Sisson
(74) *Attorney, Agent, or Firm*—Pillsbury Winthrop LLP

(57) ABSTRACT

Disclosed is a method of detecting the presence in a sample of a polypeptide exogenously administered to a mammalian subject from whom the sample is obtained, and distinguishing between such an exogenously administered polypeptide and a naturally-occurring endogenous polypeptide present in the sample; the method comprising obtaining a sample from the subject; and subjecting the sample to analysis of fluorescence at a suitable wavelength; wherein the exogenously administered polypeptide is tagged with a greater or lesser amount of fluorescence activity, relative to the untagged endogenous polypeptide, at the wavelength(s) analyzed.

10 Claims, 4 Drawing Sheets

OTHER PUBLICATIONS

Kato, C, et al. "Construction of an excretion vector and extracellular production of human growth hormone from *Escherichia coli*," *Gene*, 54 (1987) 197–202.

Pearlman, R & Bewley, T A, "Stability and Characterisation of Human Growth Hormone," *Stability and Characterisation of Proteins and Peptide Drugs: Case Histories* (eds Y John Wang and Rodney Pearlman ) (1993) Plenum Press, New York, pp. 1–58.

Smith, C J, et al, "Detection and Characterisation of Intermediates in the Folding of Large Proteins by the Use of Genetically Inserted Tryptophan Probes," *Biochemistry* 30 (4) (1991) 1028–1036.

Atkinson, T, et al, "High–level microbial expression and purification of recombinant proteins," *Bioactive Microbial Products 2* (Eds. J D Stowell, P J Bailey and D J Winstanley) (1986) Academic Press, London, pp. 27–43.

Kilhoffer et al, Biochemistry, 31:8098–8106 (1992).

Ernst and Behnke, Biochim. Biophys. Acta, 1089:331–338 (1991).

Trigo–Gonzalez et al, Biochemistry, 31:7009–7015 (1992).

Plater, Michael L. et al: "Effects of site–directed mutations on the chaperone–like activity of alpha B–crystallin" J. Biol. Chem. (1996), 271 (45), 28558–28566 CODEN: JBCHA3; ISSN: 0021–9258, XP002095857.

Chemical Abstracts (1996), 125 (15), abstract No. 186666.

* cited by examiner

vNde 1

```
GGATCCTTTTTGTTTAACTTTAAGAAGGAGATATACAT ATG CGT CCG  47
TCT ATC CAC CGT ACC GCT ATC GCT GCT GTT CTG GCT ACC  86
GCT TTC GTT GCT GGT ACC GCT CTG GCA TTC CCG ACC ATC  125
CCG CTG TCT CGT CTG TTC GAC AAC GCT ATG CTG CGT GCT  164
CAC CGT CTG CAC CAG CTG GCT TTC GAC ACC TAC CAG GAA  203
TGG GAA GAA GCT TAC ATC CCG AAA GAA CAG AAA TAC TCT  242
TTC CTG CAG AAC CCG CAG ACC TCT CTG TGC TTC TCT GAA  281
TCT ATC CCG ACC CCG TCT AAC CGT GAA GAA ACC CAG CAG  320
AAA TCT AAC CTG GAA CTG CTG CGT ATC TCT CTG CTG CTG  359
ATC CAG TCT TGG CTG GAA CCG GTT CAG TTC CTG CGT TCT  398
GTT TGG GCT AAC TCT CTG GTT TAC GGT GCT TCT GAC TCT  437
AAC GTT TAC GAC CTG CTG AAA GAC CTG GAA GAA GGT ATC  476
CAG ACC CTG ATG GGT CGT CTG GAA GAC GGT TCT CCG CGT  515
ACC GGT CAG ATC TTC AAA CAG ACC TAC TCT AAA TTC GAC  554
ACC AAC TCT CAC AAC GAC GAC GCT CTG CTG AAA AAC TAC  593
GGT CTG CTG TAC TGC TTC CGT AAA GAC ATG GAC AAA GTT  632
GAA ACC TTC CTG CGT ATC GTT CAG TGC CGT TCT GTT GAA  671
                              v Xho 1
GGT TCT TGC GGT TTC TAA CTC GAG                     695
```

Chain A

Chain B

DETECTION OF MOLECULES IN SAMPLES

This application is the national phase of international application PCT/GB98/03449 filed Nov. 16, 1998 which designated the U.S.

FIELD OF THE INVENTION

This invention relates to tagged molecules (distinguishable from untagged, but otherwise identical, molecules), methods of preparing tagged molecules, nucleic acid sequences and constructs encoding tagged molcules, and a method of distinguishing between tagged and untagged (but otherwise identical) molecules.

In particular, the present invention relates to a method of tagging a protein with a therapeutically acceptable tag which enables detection of the tagged protein administered exogenously to humans, bovines or other animals where the same (but untagged) protein is produced endogenously, and a method of detecting and differentiating the tagged protein over the endogenous protein. In particular, the method is suitable for application to human growth hormone (hGH), to enable differential detection of exogenously administered hGH in humans, for example, to determine whether hGH is being administered unlawfully for its performance enhancing effects.

BACKGROUND OF THE INVENTION

Previously, the usual method of differentiating exogenously administered protein from the endogenous one has been to tag the exogenous protein with radioactive labels. Because of the hazards of radioactivity, radioactively tagged proteins are administered to patients over short periods of time in controlled conditions and under medical supervision. Further, radioactive labels are not therapeutically acceptable since they are intrusive to the biological system in which such tagged proteins are administered. Other tagging methods tend to alter the biological function of the protein molecule and therefore are no longer suitable for therapeutic use. Such prior art tagging methods are therefore limited to controlled research uses and do not have widespread cost effective commercial applications.

Some amino acids, for example tryptophan (W) and tyrosine (Y) in particular, are natural fluorophores, which fluoresce when appropriately stimulated. This fluorescence can be detected and measured with standard prior art fluorescence detection techniques. Proteins which contain such fluorophores in their amino acid sequence may also fluoresce when appropriately stimulated. The level of fluorescence can be crudely related to the number of fluorophores in the protein. The fluorescent yield of any fluorophore is sensitive to its local environment such that, for example, there may be a difference between its fluorescence in an aqueous and a hydrophobic environment. Waldman et al (1987 Biochem. Biophys. Acta 931, 66–71; 1988 Biochem. Biophys Res. Comm. 150 (2), 752–759), Corinne (1991 Biochemistry 30, 1028–1036) and others have exploited this property to perform in vitro laboratory studies on conformational and structural changes of lactate dehydrogenase when, for example, substrate binding occurs. Waldman and Corrine have mutated lactate dehydrogenase to incorporate tryptophan residues at the substrate binding site. This technique is restricted to use as a research tool for conformational and structural studies of proteins in vitro, since often the full biological activity or structural conformation of the native protein is lost. Thus, such modified proteins are no longer suitable for therapeutic purposes and there is no disclosure or suggestion of pharmaceutical compositions comprising the mutated protein. Moreover, there is no disclosure or suggestion in the prior art that such mutations could form the basis for a method of distinguishing the altered compound from the naturally occurring compound.

WO 94/10200 discloses and is concerned with amino acid substitutions in somatotropin (i.e. Growth Hormone) which provide increased conformational and chemical stability.

There is no suggestion in WO 94/10200 that modifications can be made to Growth Hormone for the purpose of distinguishing between endogenous Growth Hormone present in a subject and exogenous Growth Hormone administered to the subject. A number of amino acid substitutions in somatotropin are disclosed or suggested in WO 94/10200 which, because of the natural fluorophore activity of the amino acid residues tryptophan and tyrosine (discussed above), result in a somatotropin molecule having an altered fluorescence activity relative to the wild type, unsubstituted molecule Such substitutions include the following:

G40→Y (i.e. glycine substituted by tyrosine at residue number 40); F52→Y: W86→F, Y, L, I or V; F103→Y; 1137→Y;

A reliable method for differentiating and detecting exogenously administered hGH is particularly desirable when attempting to monitor the pharmacokinetics and/or pharmacodynamics of hGH, or to detect its unlawful administration by athletes and others who illicitly use hGH for improving their performance. Presently, standard detection methods (e.g. HPLC, ELISA), are used for measuring the total amount of hGH in an athletes' blood or urine samples, and by subtracting the expected levels referenced to the general population, estimations of elevated hGH levels can be made. However, as levels vary considerably between individuals, and exogenous levels fall rapidly with time, this is a very crude measurement. In addition, as the performance enhancing effects last much longer than the detectable transient elevated levels of hGH in these samples, unless samples are taken shortly after administration the technique does not give indisputable proof that exogenous hGH has or has not been used.

The present invention seeks to alleviate the above mentioned problems by tagging or modifying a protein (such as hGH) with a therapeutically acceptable tag which can be detected simply and can be differentiated from the endogenous protein present in a sample of cells, blood, urine or other body fluid. The invention has little or no effect on the biological activity of the protein, such that the modified protein can be administered therapeutically in the same manner as the unmodified protein. Thus, the modified or tagged protein can be safely prescribed by physicians for existing or new therapeutic purposes, and also economically manufactured commercially at substantially the same cost as the untagged protein.

A further advantage of the present invention is that although levels of the exogenous protein may drop rapidly after administration, the specificity for the tagged protein and high sensitivity of the detection method allow detection long after the exogenous protein has been administered. Thus, an abuser cannot claim abnormally elevated production of the endogenous protein, and unlawful use of the tagged protein can be detected. Additionally, the present invention allows the pharmacokinetics and/or pharmacodynamics of the tagged exogenous protein to be detected and monitored.

Therefore, it is an object of the present invention to provide a method for tagging proteins which method enables detection of the exogenous tagged protein over any endogenous polypeptide which may be present in a sample (e.g. such as blood or urine) taken from, for example, a human subject (e.g. an athlete) or other mammalian subject (e.g. domesticated farm livestock).

It is another object of the present invention to provide a modified polypeptide molecule, such as hGH tagged in a manner which is therapeutically acceptable. Further, the tagging method of the present invention enables the biological activity per se of a protein to remain substantially unaltered such that the therapeutic efficacy is maintained and the protein can be administered in a manner identical to or similar with the unmodified protein.

A further specific object of the present invention is to provide a modified hGH molecule substituted with tryptophans at strategic positions in the native hGH sequence.

SUMMARY OF THE INVENTION

In a first aspect, the invention provides a method of detecting the presence in a sample of a polypeptide exogenously administered to a mammalian subject from whom the sample is obtained, and distinguishing between such an exogenously administered polypeptide and a naturally-occurring endogenous polypeptide present in the sample; the method comprising obtaining a sample from the subject; and subjecting the sample to analysis of fluorescence at a suitable wavelength; wherein the exogenously administered is tagged with a greater or lesser amount of fluorescence activity, relative to the untagged endogenous polypeptide, at the wavelength(s) analysed.

In a second aspect, the invention provides a composition for administration to a mammalian subject, the composition comprising a polypeptide and a physiologically acceptable carrier substance, characterised in that the polypeptide is tagged with a greater or lesser amount of fluorescent activity relative to an untagged polypeptide endogenously present in the subject, the tagged molecule thereby being distinguishable from the untagged molecule by analysis of the fluorescence characteristics of the respective molecules, excluding those compositions in which the tagged molecule is Growth Hormone and wherein the fluorescent tagging consists solely of one or more of the following substitutions in the tagged Growth Hormone:

G40→Y: F52→Y; W86→F, Y, L, I or V; F103→Y; and 1137→Y.

The tagged molecule is a polypeptide, which may typically be administered to a mammalian subject to exert a beneficial effect (e.g. for clinical or veterinary reasons, or for reasons of animal husbandry). The mammalian subject will generally be human, but may also be a domesticated animal, especially a farm animal such as a bovine, porcine or ovine animal. The tagged molecule will generally therefore be a therapeutic polypeptide (i.e. comprises five or more amino acid residues and has a desirable effect on the subject, with little or no undesired side effect, when administered in an appropriate dose) and will possess the same biological activity as, and normally be substantially identical (except for the tagging) to, a naturally-occurring polypeptide present in the subject, although where the tagged molecule is a recombinant polypeptide it may have additional slight differences relative to the naturally occurring polypeptide (e.g. to increase activity, or to increase stability, e.g. as taught in WO 94/10200). (The "biological activity" of the molecule is that activity by which the molecule exerts its beneficial effect on the subject e.g. stimulation of growth in the case of GH; or stimulation of erythrocyte production in the case of EPO.)

The molecule may be, for example, a pharmaceutical. A particularly preferred molecule is a mammalian growth hormone, especially human growth hormone (hGH), bovine growth hormone (bGH), or porcine growth hormone (pGH); or calcitonin; or erythropoietin (EPO). Accordingly it is preferred that any fluorophores present in the tagged molecule: (a) do not have any significant effect on the biological activity of the molecule; and (b) are essentially non-toxic (that is, any fluorophores present will not cause the tagged molecule to exhibit any toxicity for the subject when the molecule is administered at normal therapeutic doses). Accordingly, tryptophan or tyrosine and closely-related compounds are preferred fluorophores for use in tagged molecules in accordance with the invention. These have the additional advantage of being readily incorporated into polypeptide molecules.

Advantageously, the tagged molecule is either deficient in, or comprises additional, fluorescent entities (fluorophores) relative to the untagged molecule. The tagging may therefore be "positive" (in which the tagged molecule comprises additional fluorophores) or "negative" (where the tagged molecule is deficient in fluorophores relative to the untagged molecule).

As explained above, the naturally occurring amino acid residues tryptophan (W) and, to a lesser extent tyrosine (Y), possess natural fluorophore activity. Thus, if an "untagged" polypeptide comprises one or more tryptophan and/or tyrosine residues it may be fluorescent. Thus a tagged molecule, in accordance with the invention, may be distinguishable from an untagged molecule by having additional fluorophores (especially if the untagged polypeptide comprises no, or very few, tryptophan or tyrosine residues and thus possesses no, or very little, intrinsic fluorescence). Alternatively, where the untagged molecule comprises a fluorophore (especially a plurality of fluorophores), the tagged molecule may be distinguishable by having fewer fluorophores than the untagged molecule.

Preferably, the tagged molecule comprises additional fluorophores present in amino acid residues or other compounds which are capable of forming a peptide bond, and thus are capable of being covalently incorporated into a polypeptide, either internally during synthesis of the polypeptide, and/or at the C-terminal after synthesis of the bulk of the polypeptide.

Conveniently the fluorophores additionally present in (or absent from) the tagged molecule (relative to the untagged molecule) are tyrosine and/or tryptophan residues, or a synthetic amino acid derivative wherein a fluorophore is covalently joined to an "amino acid" backbone, the synthetic derivative having the general formula

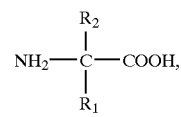

wherein $R_1$ comprises the fluorophore and $R_2$ is H, OH, halide or lower alkyl ($C_1$ to $C_3$, substituted or unsubstituted). The fluorophore $R_1$ may be a fluorophore which is present in a naturally occurring amino acid residue (e.g. the aromatic groups of tryptophan or tyrosine) or may be some other fluorophore (typically comprising a delocalised electron system, such as in an aromatic or heterocyclic ring). Such synthetic amino acid derivatives are already known in the art or can readily be prepared using standard organic chemistry techniques.

As a less preferable alternative to the tagged molecule comprising a different number of fluorophores (relative to the untagged molecule), the tagged molecule may comprise the fluorophores at different positions—the immediate chemical environment can affect the level of fluorescence of a fluorophore. Accordingly, the tagged molecule may not have a different number of fluorophores relative to the untagged molecule, but they may be of different fluorescent activities and/or be differently disposed within the molecule so as to affect their fluorescence.

Where the tagged molecule is a polypeptide, tagging is conveniently accomplished by substituting a non-fluorescent amino acid present in the untagged molecule for an amino acid residue comprising a fluorophore (such as tryptophan, tryosine or a synthetic amino acid derivative), so as to increase the fluorescence of the tagged molecule relative to the untagged molecule.

With the benefit of the teaching of the present specification, and with the benefit of information otherwise readily available as common general knowledge, the person skilled in the art can, by routine trial and error, find appropriate amino acid residues which can be substituted, without substantially affecting the biological activity of the molecule. Conveniently, phenylalanine residues (F) or tyrosine residues (Y) can be replaced with tryptophan residues (W), which exhibit far greater fluorescence activity. Such substitutions are "conservative" and thus tend not to have any significant effect on the biological properties of a polypeptide. Further guidance for the person skilled in the art is given in the example below, which utilises principles which are generally applicable to any biologically active polypeptide.

The composition will normally comprise an effective amount of the tagged molecule, such that the biological activity thereof produces a demonstrable effect when administered to the subject. An "effective amount" is the amount of tagged molecule which results in the desired biological effect in the mammalian subject to which the composition is administered. The desired effect will, of course, depend on the identity of the tagged molecule: where the tagged molecule is EPO, for example, the desired effect is an increase in the number of erythrocytes per unit volume of blood in the subject. In some embodiments the composition will be essentially sterile, and suitable for delivery by means of injection (e.g. by transdermal, intravenous, intramuscular or subcutaneous routes). In other embodiments the composition will be in the form of a tablet, pill or capsule (e.g. enteric-coated capsules for slow release) for oral consumption.

Administration of the compositions of the invention into a mammalian subject may be performed according to known methods using any route effective to deliver the required dosage to the subject. Modes of administration include those typically encountered for the species of choice. Because proteins in general are susceptible to degradation in the digestive system, injection is preferred via an intramuscular, transdermal or subcutaneous route. The use of sustained or prolonged release formulations or implants are also suitable modes. Generally, injection of a sustained release formulation is preferred.

The effective dosage range depends on the species, age, weight, and general health of the mammalian subject. These and other parameters which are needed to determine the effective dosage range for a given mammal are well within the purview of one skilled in the art. For instance, in bovines the effective amount of bovine GH (whether tagged or untagged) is in the range of 1.0 to 200 milligrams per animal per day. In pigs, for instance the effective amount of porcine GH is about 60 $\mu$kg/day.

The physiologically acceptable carrier may be a sterile liquid diluent where the composition is injected (e.g. saline, phosphate-buffered saline, or other aqueous buffer preparation). Where the composition is to be administered orally or transdermally, the carrier may be calcium carbonate, calcium sulphate or other substantially inert solid. Transdermal delivery by means of a needleless injection device may generally be preferred.

Methods of performing the fluorescence analysis may be entirely conventional and well known to those skilled in the art (e.g. spectrofluorimetry). The choice of method will depend in part on the manner in which the exogenous substance is tagged, and the characteristics of the fluorophore (if any) employed in the tagged molecule. For example, where the tagged molecule comprises fewer or more tryptophan residues than the untagged molecule, fluorescence analysis will typically be performed at about 297 nm excitation.

Advantageously the sample is subjected to processing, prior to fluorescence analysis, to enrich or purify the endogenous and (if present) exogenous molecules in the sample. This improves the signal-to-noise ratio. Various methods of enrichment or purification may be employed, using one or more of the following techniques: centrifugation: HPLC: FPLC; affinity chromatography; immunoaffinity chromatography; heat treatment at 50–55° C. for ten minutes (this is particularly appropriate for purification of growth hormone, which is relatively heat-stable—contaminating proteins will tend to be denatured, aggregate and precipitate, and so can be simply removed by centrifugation whilst the undenatured growth hormone stays in solution); all of which are well known to those skilled in the art. The preferred method may depend, at least in part, on the identity of the endogenous and exogenous molecules.

The method defined immediately above is extremely useful in detecting the presence of exogenously administered molecules used illicitly by cyclists, athletes and others to improve performance. Very often, such molecules occur naturally (e.g. EPO, hGH, and the like) and are endogenous to the athlete's body, such that proving illicit use of performance-enhancing substances is very difficult. However, with the benefit of the present invention, such substances can be tagged, and thus made distinguishable over endogenous molecules synthesised naturally in the athlete's body.

Additionally the invention can be used to monitor the persistence of substances administered to the body. For example, the pharmacokinetics and/or pharmacodynamics of various drugs can readily be monitored by comparing fluorescence activities at different time points—this is particularly useful where the tagged drug is otherwise identical to an endogenous compound.

In a preferred embodiment, the tagged molecule is a polypeptide prepared using recombinant DNA technology. In such embodiments the method may additionally comprise the preparation of a nucleic acid sequence encoding the tagged molecule, the sequence being mutated relative to the wild type sequence encoding the untagged molecule. Typically the nucleic acid sequence encoding the tagged polypeptide comprises nucleotide substitutions (relative to the wild type sequence) so as to direct the expression of a polypeptide having one or more tryptophan residues not present in the untagged molecule or, less preferably, directing the expression of a polypeptide having fewer tryptophan residues than in the untagged molecule.

The nucleic acid sequence encoding the tagged molecule may be prepared, for example, by mutation of the wild-type sequence (e.g. by site-directed mutagenesis), by polymerase chain reaction (PCR), or by de novo synthesis (e.g. using an automated DNA synthesiser). All of these techniques are familiar and well-known to those skilled in the art and/or are readily obtained by reference to standard texts in the field (e.g. Sambrook et al, "Molecular Cloning, A Laboratory Manual" Cold Spring Harbor Laboratory Press, 1989).

Where the subject is a human, the sample may conveniently be a sample of body fluids, such as a blood, sweat, semen, urine, or saliva sample. Less preferably the sample may be a tissue sample comprising cells (e.g. skin scrapings from the buccal cavity, hair or the like). Where the subject is a domesticated farm animal, the sample may be taken from the animal before or after slaughter. Samples taken after slaughter conveniently include muscle tissue or other solid tissues taken from the carcass.

In another aspect of the present invention there is provided a tagged GH molecule comprising a tryptophan residue substituted for a phenylalanine residue present in a naturally-occurring molecule. In one embodiment, tryptophan is substituted at positions F31 and/or F97 in the amino acid sequence.

In a preferred embodiment, the tagged growth hormone comprises a tryptophan residue at one or more of positions 10, 31, 97, 160 or 176 (of which tryptophan residues at positions 31 and/or 97 are especially preferred). The tagged growth hormone molecule is preferably tagged hGH.

According to a still further aspect of the present invention there is provided a nucleic acid expression vector comprising substantially nucleotides 114–695 of the nucleic acid sequence shown in FIG. 2. The $CPG_2$ signal sequence (nucleotides 39–113) is intended to direct the encoded polypeptide product to the bacterial periplasm—those skilled in the art will appreciate that the $CPG_3$ signal does not form an essential part of the vector, but is useful for expression in prokaryotes. Other signal sequences are well known to those skilled in the art and could be substituted for the $CPG_2$ signal sequence if desired. Thus the expression vector may be designed to cause expression in eukaryotes (e.g. mammalian tissue culture, fungal or yeast cultures) or in prokaryotes (bacterial cultures). In a particular embodiment the expression vector is a prokaryotic expression system, preferably comprising the vector pMTLhGHm described below.

The invention will now be described by way of illustrative examples and with reference to the accompanying drawings, in which:

FIG. 1 shows the primary amino acid sequence (Seq. ID No. 1) of native hGH protein;

FIG. 2 shows a nucleic acid sequence (Seq. ID No. 2) encoding a tagged hGH molecule for use in the method of present invention:

FIG. 3 shows the primary amino acid sequence (Seq. ID No. 3) of the tagged hGH molecule encoded by the nucleic acid sequence of FIG. 2;

FIG. 5 shows the amino acid sequence of human calcitonin (Seq. ID No. 4)—the sequence is shown in the orientation N terminal→C terminal, but the C terminal residue includes a naturally occurring amide group (as a post-translational modification);

FIG. 6 shows the amino acid sequence of human growth hormone releasing factor (HGHRF) (Seq. ID No. 5)—the sequence is shown in the orientation N terminal→C terminal, but the C terminal residue includes a naturally occurring amide group (as a post-translational modification);

FIGS. 7A and 7B show the amino acid sequence of the A and B chains respectively of human insulin (Seq. ID Nos. 6 and 7);

Figures 7A, 7B, 8, 9:
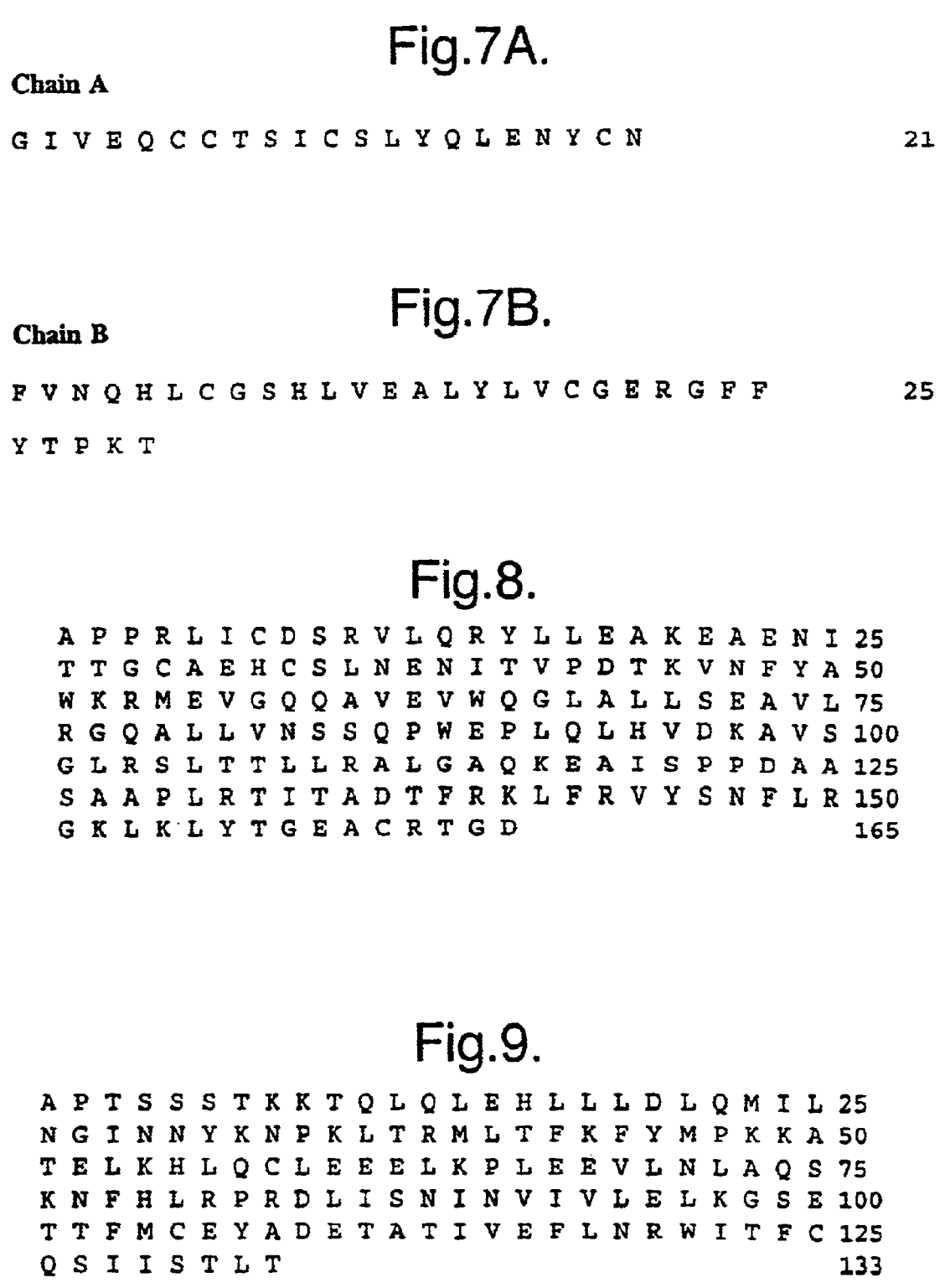
Figure 4:
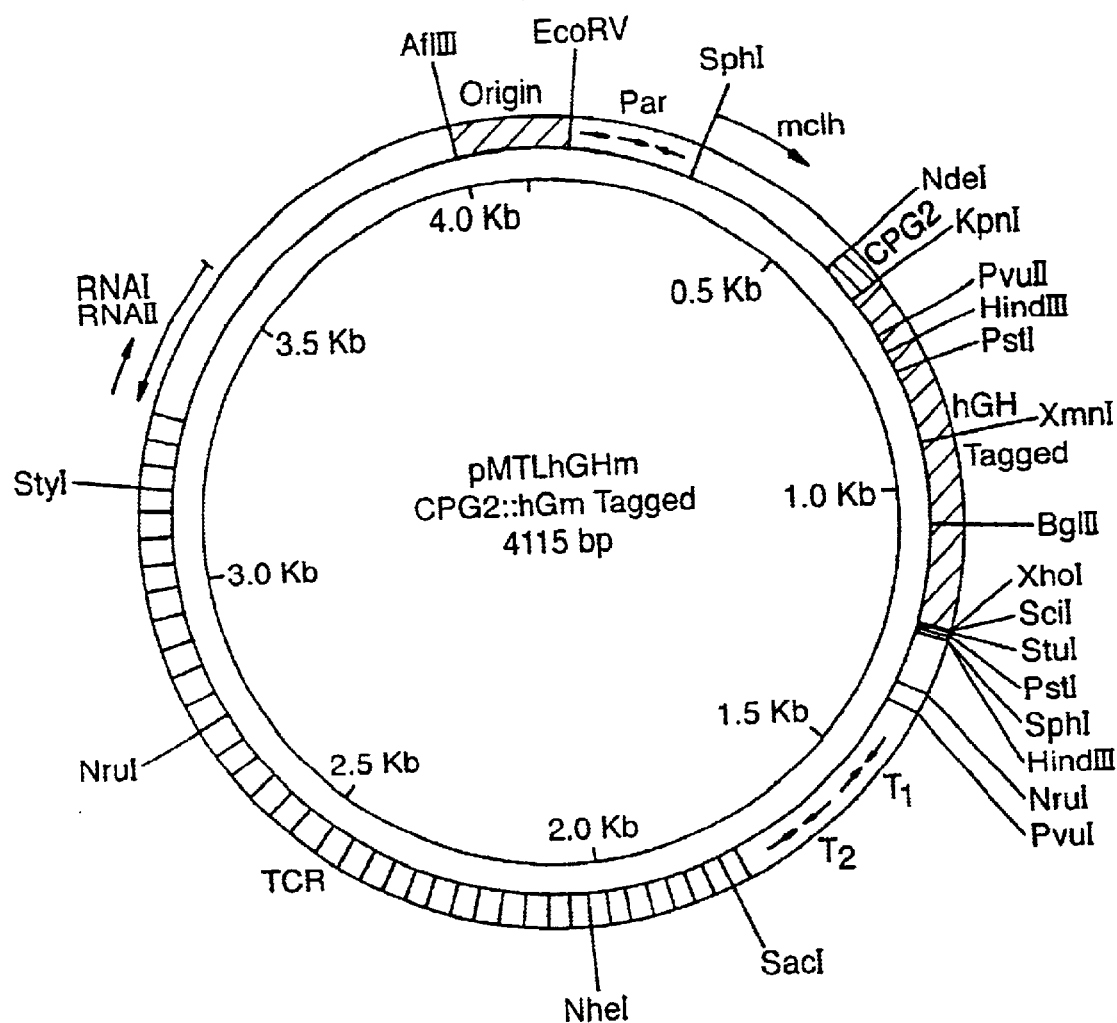
FIG. 4 is a schematic representation of the nucleic acid construct pMTLhGHm used to express a tagged polypeptide in accordance with the invention.

FIG. 8 shows the amino acid sequence of human Erythropoietin (Seq. ID No. 8); and FIG. 9 shows the amino acid sequence of human Interleukin 2 (Seq. ID No. 9).

EXAMPLE 1

Construction of an Enhanced Fluorescent Form of hGH

Amino acids can be generally classified into 4 main classes depending on their R groups: (1) non-polar or hydrophobic R groups; (2) neutral (uncharged) polar R groups; ((3) positively charged R groups; and (4) negatively charged R groups.

Although within any single class there is considerable variation in the size, shape, and properties of the R groups, certain amino acids show similar properties and can often be substituted without dramatically changing the protein conformation or biological activity. It has been suggested that there is a 70–80% chance of attaining a mutated protein with unchanged biological properties, by replacing any one phenylalanine (F) or tyrosine (Y) residue by tryptophan (W). However, it is not always possible accurately to predict the actual effect of such substitutions on the conformation and/or biological activity of a protein. The extent of the effect or sensitivity of the protein to such substitution(s), will depend on the function of the target amino acid residue which is to be substituted. If the target amino acid is involved in catalysis or interacts with another residue, the protein will be sensitive to substitution. However, if the target amino acid is a scaffolding residue, the protein will be less sensitive to substitution by an amino acid with a similar R group.

Figures 1, 2:
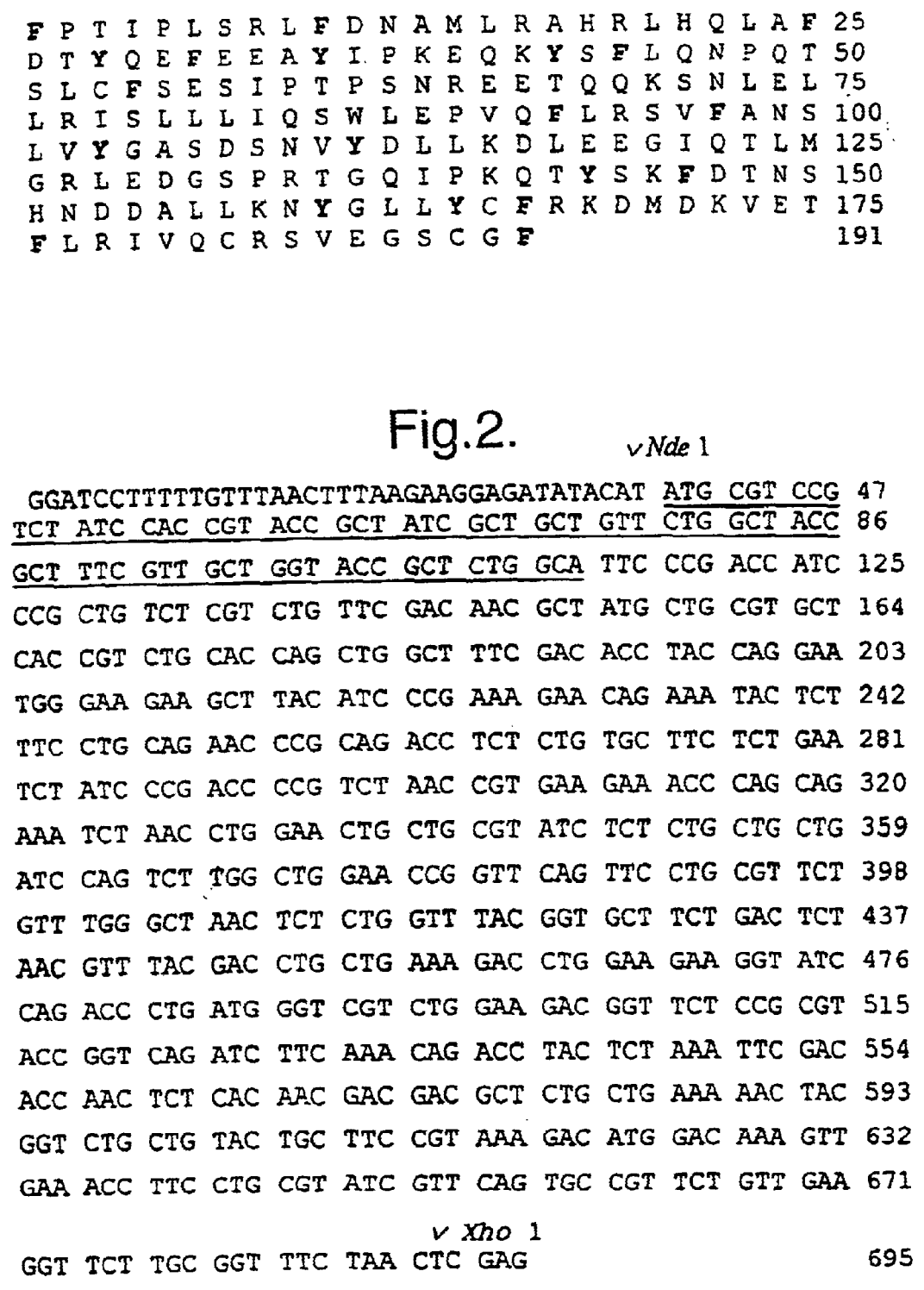

In the native hGH amino acid sequence, there are twelve F, eight Y and one W residues (see FIG. 1). In the method described below, techniques available in the art are used to establish which of the F and Y residues will have the least effect on the structure and biological activity of hGH, if substituted with W.

Determination

Using the available 3D X-ray structures of hGH alone and hGH complexed with its receptor (both obtained from the Brookhaven data base) the positions of twenty potential substitutions were analysed in order to filter out the sensitive substitutions by Environmental Filtering which involves:

1) Eliminating Residues Close to the Surface of the Protein:

The inventors find that substitutions at surface sites should be avoided since the added hydrophobic character of the tryptophan residue sometimes gives rise to increased protein aggregation. Further, modifications to residues at the surface of a polypeptide are generally undesirable as they may (i) interfere with binding activity of the protein; and (ii) are more likely to create a new epitope which may be recognised as foreign by the immune system of the recipient. The following residues were shown to be surface residues and were therefore regarded as poor candidates for substitution in hGH:-F1: F25; Y35; Y42; F44; F54; F92; Y103; Y111; Y143; F146; F191.

2) Eliminating Residues Close to Inter-protein Surfaces:

The remaining eight residues were determined to be buried in the protein conformational structure. Y164 and Y28 were determined to have close proximity to the hGH receptor glutamate residue and therefore likely to be critical in the interaction between hGH and its receptor. Thus, residues Y164 and Y28 are poor candidates for substitution.

3) Eliminating Residues Close to W86:

It is known that fluorophores which are in close proximity to each other can interact through internal energy transfer (a blue shift in emission) thereby quenching the individual fluorescence of each fluorophore. F166 was determined to be in close proximity to W86, the single naturally occurring fluorophore in the native hGH protein. In order to avoid such potential quenching effects which could reduce the desired effect of fluorescence enhancement of the mutated protein, F166 was regarded as a poor candidate for substitution.

From the above analysis the inventors determined that the best candidates for W substitutions are: F31, F97, F10, F176 and/or Y160. Further analysis of the environmental position of these five residues within the native hGH revealed suitability for W substitution (see Table 1). In the example given below, F31 and F97 were selected for construction of the modified protein, and the other remaining residues are potentially suitable candidates also. It will be appreciated that other amino acids at suitable sites may be similarly substituted, and that, whilst substitution of F or Y residues is preferred, the invention is not so limited.

Table 1 shows the five tryptophan substitutions predicted as least likely to alter the hGH protein conformation and therefore least likely to affect biological activity.

| RESIDUE | ENVIRONMENT | DISTANCE TO RECEPTOR SURFACE |
| --- | --- | --- |
| F31 | Hydrophobic cluster just below surface. Between helices. | Great |
| F97 | Deep in a surface cleft | Great |
| F10 | Hydrophobic surface slot | Adequately remote |
| F176 | Buried, but close to W86 | Adequately remote |
| Y160 | Hydrophobic cluster just below the surface | About 0.6 nm from receptor surface |

The principles described above (i.e. avoiding substitution of residues which are surface-exposed or near functional sites such as active or allosteric sites of enzymes or receptor-binding sites of ligands; and avoiding substitution of residues near other fluorescent residues) can be used to identify phenylalanine residues in any other biologically active molecule which are suitable for substitution by tryptophan, thereby allowing any desired polypeptide to be tagged, relative to a naturally-occurring endogenous polypeptide, so that the method of the invention can be applied very generally.

EXAMPLE 2

Construction of Gene by Substituting W for F31 and 97

Optimised gene sequence: Using the empirically observed codon utilisation bias for highly expressed $E.$ $coli$ genes, the known DNA sequence coding for native hGH was re-designed incorporating, where possible, this $E.$ $coli$ codon bias whilst ensuring retention of the original translated protein sequence. The two substitutions (W31 and W97) were then incorporated into this optimised $E.$ $coli$ gene sequence. It will be appreciated by those skilled in the art that optimisation of codon bias for $E.$ $coli$ may not be desirable if the sequence is to be expressed in a host other than $E.$ $coli$.

FIG. 2 shows the nucleotide sequence used to encode the modified hGH. To facilitate expression and subsequent purification, the hGH coding sequence is preceded by a 75 bp fragment of DNA derived from the carboxypeptidase $G_2$ ($CPG_2$) gene encoding the twenty-five amino acid signal peptide of $CPG_2$ (Minton et al, 1985 Gene 31, 31–38). The $CPG_2$ signal peptide directs the expressed protein to the periplasm where the $CPG_2$ signal sequence is enzymatically cleaved, releasing the authentic hGH protein into the periplasm. Those skilled in the art will appreciate that the $CPG_2$ signal peptide sequence could be replaced with any one of a large number of functionally equivalent signal sequences from other sources, without substantially affecting the nature of the construct.

Figures 3, 5, 6:
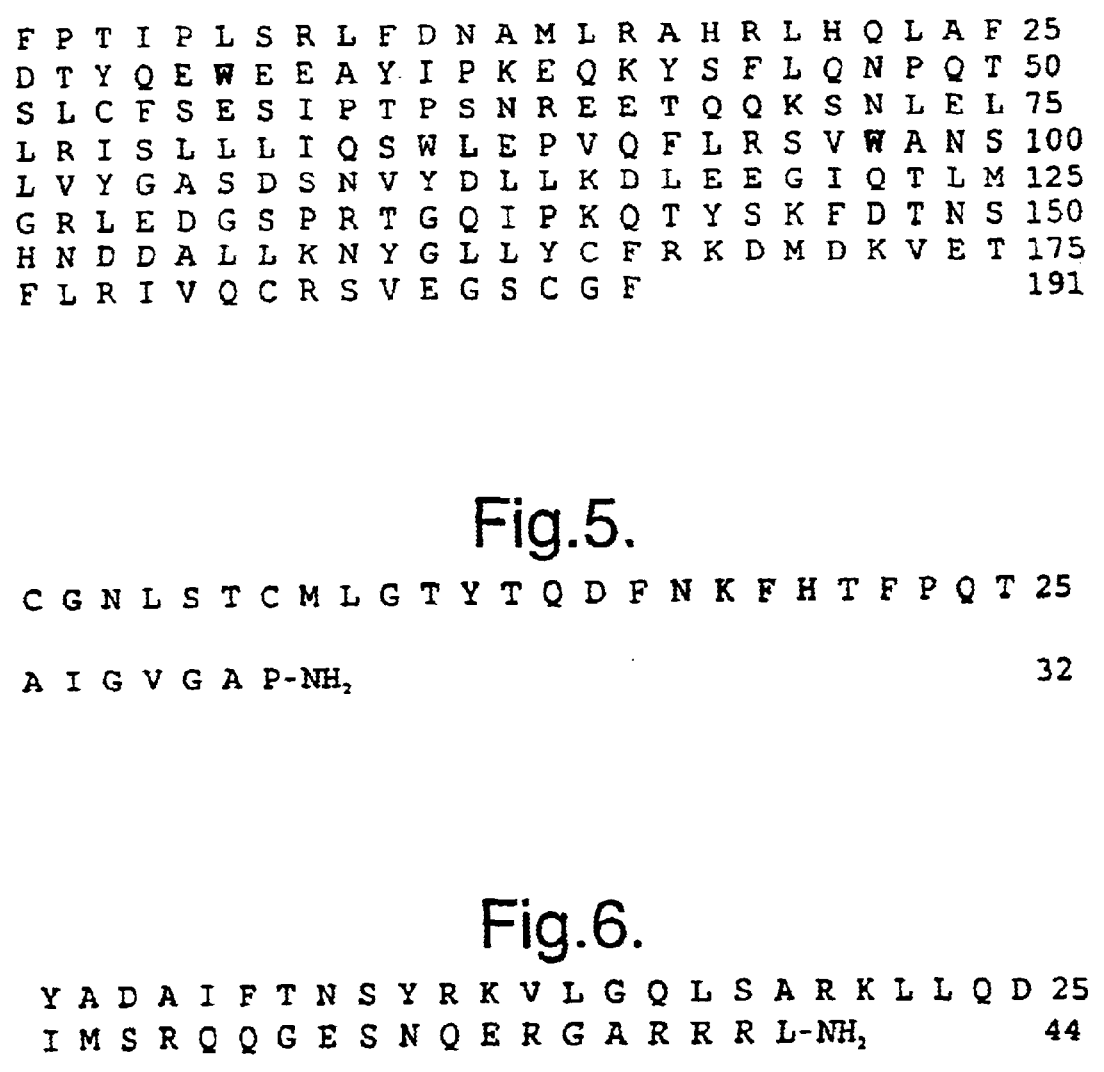

The amino acid sequence of the tagged hGH encoded by the nucleic acid sequence is shown in FIG. 3; the tryptophan substitutions at positions 31 and 97 are shown in bold type.

Construction of the synthetic gene: This synthetic gene was constructed by standard chemical procedures (Wosnick et al, 1987 Gene 60 (1), 115–127) using double-stranded annealed pairs of 60–100 bp oligonucleotides with appropriately compatible sticky ends.

Cloning: Using standard techniques, the synthesised gene was restricted with Nde I and Xho 1 and cloned into the identical restriction sites of pMTL1015 (Chambers et al, 1986 Gene 68(1), 139–149) to produce pMTL hGHm (illustrated schematically in FIG. 4). This vector directs expression of the synthetic gene under the control of the mdh promoter (Alldread et al, 1992 Gene 114(1), 139–143), and carries a selectable tetracycline resistance gene ($Tc^R$). Those skilled in the art will appreciate that the mdh promoter could be replaced with any one of a large number of functionally equivalent promoters from other sources, without substantially affecting the nature of the construct.

The new construct, pMTLhGHm, was transformed and subsequently expressed in an appropriate strain of $E.$ $coli$ (K-12 strain RV308, ATCC 31608) using standard procedures.

Production and Purification: The modified hGH protein (hGH) may be produced in an industrial scale fermenter by methods well known to those skilled in the art. For example, a transformed $E.$ $coli$ culture containing pMThhGHm may be grown up in aqueous media in a steel or other fermentation vessel conventionally aerated and agitated, in aqueous media at e.g. about 28–37° C. and near neutral pH, supplied with appropriate nutrients such as glycerol, nitrogen sources such as ammonium sulphate, potassium sources such as potassium phosphate, trace elements, magnesium sulphate and the like. The plasmid pMTLhGHm carries tetracycline resistance as a selectable characteristic, so that selection pressure (i.e. inclusion in the medium of tetracycline at 12.5 $\mu$g/ml) may be imposed to discourage competitive growth from wild-type organisms which lack the resistance characteristic (e.g. due to "segregation" of the plasmid during growth of the culture).

Upon completion of fermentation the cell suspension is centrifuged or the cellular solids otherwise collected from the broth and then lysed by physical or chemical means. Cellular debris is removed from supernatant and soluble hGHf isolated and purified.

HGHf may be purified from cell extracts using one or more of the following techniques: (i) polyethyleneimine fractionation; (ii) gel filtration chromatography on Sephacryl S-200: (iii) ion exchange chromatography on ToyoPearl Super Q 650 m or CM Sephadex; (iv) hydrophobic chromatography using Phenyl-Sepharose: (v) ammonium sulphate and/or pH fractionation: (vi) selective heat enrichment; and (vii) affinity chromatography using antibody resins prepared from anti-hGM IgG isolated from immunosensitised animals or hybridomas; and desorbed under acid or slightly denaturing conditions. In particular, recombinant Growth Hormone may be purified from $E.$ $coli$ cultures according to the method disclosed in WO 87/00204 or EP 0 177 343.

EXAMPLE 3

Fluorescence Detection

In order to detect the bGHf by fluorescent measurements in samples from a mammalian subject to whom the hGHf has been administered, it is preferable to purify or enrich the sample (i.e. blood or urine) to reduce background fluorescent interference. This can be routinely accomplished by the use of a number of standard chromatographic techniques such as HPLC, FPLC, affinity chromatography, or immunoaffinity chromatography. Fluorescence may be increased by prior denaturation of the protein, for example by use of mild heat treatment and/or chaotropic agents (e.g. 1–6M Urea or guanidimium chloride).

W-fluorescence is measurable using standard techniques such as, for example, an SLM 8000 single photon counting spectrofluorometer. The purified sample is subjected to excitation around 297 nm across a 2 mm cell using a mercury-Xenon arc lamp and fluorescence detected around 345 nm using a Mullard XP 2020Q rapid-response photomultiplier along a 1 cm path at 90° to the excitation beam. Scattered light is excluded by cut-off filter (Schott 310) between the sample and photomultiplier.

An alternative embodiment of the invention can be envisaged, in which exogenous hGH is provided with reduced fluorescence relative to the naturally occurring molecule, for example by replacing W at position 86 with either F or Y.

It will be appreciated that the present invention has applications in other areas such as detection of exogenous proteins over the same protein produced endogenously, for example, measuring exogenous bovine growth hormone (bGH) which is administered to increase milk or meat production in cattle. Additionally the methods of the present invention can be used to detect abuse of such anabolic proteins in humans or in animals.

It will be further appreciated that the present invention is not limited to mammalian growth hormone proteins and can be equally successfully applied to other proteins including those which are also produced endogenously and those with therapeutic applications, such as calcitonin.

EXAMPLE 4

Human Calcitonin

Calcitonin (thyrocalcitonin) is an endogenous 32 amino acid peptide hormone produced by certain cells in the thyroid gland whose principle action is to lower the levels of calcium and phosphate in the blood. It is used clinically to treat several disorders such as hypercalcaemia and bone disorders such as Paget's disease and Osteoporosis. The amino acid sequence of calcitonin is illustrated in FIG. 5, and included as Seq. ID No. 4 in the attached Sequence Listing.

Calcitonin may be negatively tagged (i.e. provided with reduced fluorescence) or positively tagged (i.e. provided with reduced fluorescence) relative to the naturally occurring molecule as follows:

To reduce fluorescence: replace Y 12 with L;

To increase fluorescence any one of the following substitutions may be performed: replace Y 12 with W; replace any F residue (located at positions 16, 19, and 22) with W; replace any two F residues (located at positions 16, 19, and 22) with W, preferably F 16 and F 22 (so as to avoid possible complications of "quenching" or other interference if fluorophores are too close together), replace any F residue (located at positions 16, 19, and 22) with Y, preferably F 22; replace any two F residues (located at positions 16, 19, and 22) with Y, preferably F 16 and F 22.

EXAMPLE 5

Human Growth Hormone Releasing Factor

Human Growth Hormone Releasing Factor (HGHRF) is an endogenous 44 amino acid peptide hormone that controls the release of human growth hormone. Consequently its clinical uses are similar to those for human growth hormone itself. The amino acid sequence of HGHRF is shown in FIG. 6, and included as Seq. ID No. 5 in the attached sequence listing. HGHRF may be positively tagged (i.e. provided with increased fluorescence) relative to the naturally occurring molecule, by performing any one of the following substitutions: replace any one of R 41, 42, or 43 with W; or replace both R 41 and R 43 with W.

EXAMPLE 6

Human Insulin

Human insulin is an endogenous hormone produced in the pancreas by the beta cells of the islets of Langerhans and is important for regulating the amount of glucose in the blood. Lack of this hormone gives rise to diabetes mellitus, and as such insulin is used clinically to treat this condition. Mature insulin consists of two peptides, termed A and B, which are joined by two disulphide bridges: one between A chain C7 and B chain C7; and a second between A chain C20 and B chain C19. The sequence of the A and B chains of human insulin are shown in FIGS. 7A and 7B respectively, and are included as Seq. ID Nos. 6 and 7 in the attached sequence listing.

Human insulin may be negatively tagged or positively tagged, relative to the naturally occurring molecule, so as to be provided with reduced or increased fluorescence respectively, as described below:

To reduce fluorescence: replace any one or more Y residues (located at positions A 14; B 16 B 26) with either L or F;

To increase fluorescence: either; replace any F residue (located at positions B 24 and B 25) with W; replace any Y residue (located at positions A 14; B 16; and B 26) and either F residue (located at positions B 24 and B 25) with W.

EXAMPLE 7

Human Erythropoietin (EPO)

Human Erythropoietin is the principal endogenous factor responsible for the regulation of red blood cell production during steady-state conditions and for accelerating recovery of red blood cell mass following haemorrhage. As a result, EPO has important clinical uses where elevated levels of red blood cell expression is indicated. The amino acid sequence of EPO is shown in FIG. 8, and is included as Seq. ID No. 8 in the attached sequence listing. EPO may conveniently be negatively tagged relative to naturally occurring EPO by replacing any one or more W residues (located at positions 51, 64 and 88) with F.

EXAMPLE 8

Human Interleukin 2 (IL2)

Human Interleukin 2 is an endogenous factor produced and secreted primarily by activated T helper cells that acts as a paracrine factor driving the expansion of antigen specific cells and as a paracrine factor influencing the activity of a number of other cells including B cells. NK cells and LAK cells. Because of this central role of the IL-2/IL-2R system in mediation of the immune response, IL-2 has important diagnostic and therapeutic implications.

For example, IL-2 has shown promise as an anti-cancer drug by virtue of its ability to stimulate the proliferation and activities of tumour-attacking LAK and TIL cells. The amino acid sequence of human IL-2 is shown in FIG. 9 and is included as Seq. ID No. 9 in the attached sequence listing.

Human IL-2 may conveniently be negatively tagged or positively tagged (i.e. provided with reduced or increased fluorescence, respectively) relative to naturally occurring IL-2 as follows:

To reduce fluorescence: replace W 121 with either Y or F;

To increase fluorescence: either; replace any one or more F residues (located at positions 42, 44, 78, and 103) with W; or replace any one or more Y residues (located at positions 31, 45 and 107) with W.

What is claimed is:

1. A method of detecting the presence in a sample of a polypeptide exogenously administered to a mammalian subject from whom the sample is obtained, and distinguishing between such an exogenously administered polypeptide and a naturally-occurring endogenous polypeptide present in the sample; the method comprising obtaining a sample of body fluid from the subject; and subjecting the sample to analysis of fluorescence at a suitable wavelength; wherein the sample is subjected to processing, prior to analysis, by one or more of the following: centrifugation; HPLC; FPLC; affinity chromatography; immunoaffinity chromatography; denaturation or heat treatment, so as to enrich or purify the exogenous polypeptide thereby to improve the signal:noise ratio; and wherein the exogenously administered polypeptide has a greater or lesser amount of fluorescence activity, relative to the endogenous polypeptide, at the wavelength(s) analysed, wherein the greater or lesser amount of fluorescence activity is due to the respective presence or absence in the exogenously administered polypeptide, relative to the endogenous polypeptide, of a fluorescent amino acid residue or a synthetic amino acid derivative in the amino acid backbone of the polypeptide, the synthetic amino acid derivative having the formula

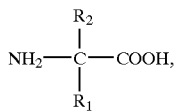

wherein R₁ comprises the fluorophore and R₂ is H, OH, halide or substituted or unsubstituted lower alkyl; and wherein the exogenously administered polypeptide comprises human, bovine or porcine growth hormone.

2. A method according to claim 1, wherein the sample is subjected to processing, prior to fluorescence analysis, to enrich or purify the exogenous and endogenous molecules in the sample.

3. A method according to claim 1, wherein the sample comprises one or more of the following: blood; saliva; urine; semen; or tears.

4. A method according to claim 1, wherein the exogenously administered polypeptide has greater fluorescence activity, at the wavelength analysed, than the endogenous polypeptide.

5. A method according to claim 1, wherein the exogenously administered polypeptide comprises one or more fluorophores not present in the endogenous polypeptide.

6. A method according to claim 5, wherein a compound comprising a tagging fluorophore is incorporated in the exogenously administered polypeptide by means of a peptide bond.

7. A method according to claim 5, wherein the fluorophore comprises tyrosine or tryptophan.

8. A method according to claim 1, wherein the exogenously administered polypeptide comprises human growth hormone.

9. A method according to claim 1, wherein the exogenously administered polypeptide comprises growth hormone tagged with a tryptophan residue at one or more positions 10, 31, 97, 160 or 176.

10. A method according to claim 1, wherein the endogenously administered polypeptide comprises a substitution, relative to the endogenous polypeptide, of one or more phenylalanine or tyrosine residues with a corresponding number of tryptophan residues.

* * * * *

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 191 amino acids
      (B) TYPE: amino acid
      (C) STRANDEDNESS: single
      (D) TOPOLOGY: linear (xi) SEQUENCE DESCRIPTION: SEQ ID NO: 1:

```
Phe Pro Thr Ile Pro Leu Ser Arg Leu Phe Asp Asn Ala Met Leu Ar
1               5                   10                  15

Ala His Arg Leu His Gln Leu Ala Phe Asp Thr Tyr Gln Glu Phe Gl
            20                  25                  30

Glu Ala Tyr Ile Pro Lys Glu Gln Lys Tyr Ser Phe Leu Gln Asn Pr
            35                  40                  45

Gln Thr Ser Leu Cys Phe Ser Glu Ser Ile Pro Thr Pro Ser Asn Ar
        50              55                  60

Glu Glu Thr Gln Gln Lys Ser Asn Leu Glu Leu Leu Arg Ile Ser Le
65                  70                  75                  80

Leu Leu Ile Gln Ser Trp Leu Glu Pro Val Gln Phe Leu Arg Ser Va
            85                  90                  95

Phe Ala Asn Ser Leu Val Tyr Gly Ala Ser Asp Ser Asn Val Tyr As
            100                 105                 110

Leu Leu Lys Asp Leu Glu Glu Gly Ile Gln Thr Leu Met Gly Arg Le
            115                 120                 125

Glu Asp Gly Ser Pro Arg Thr Gly Gln Ile Pro Lys Gln Thr Tyr Se
            130                 135                 140

Lys Phe Asp Thr Asn Ser His Asn Asp Asp Ala Leu Leu Lys Asn Ty
145                 150                 155                 160

Gly Leu Leu Tyr Cys Phe Arg Lys Asp Met Asp Lys Val Glu Thr Ph
                165                 170                 175

Leu Arg Ile Val Gln Cys Arg Ser Val Glu Gly Ser Cys Gly Phe
            180                 185                 190
```

(2) INFORMATION FOR SEQ ID NO: 2:

(i) SEQUENCE CHARACTERISTICS:
      (A) LENGTH: 695 base pairs
      (B) TYPE: nucleic acid
      (C) STRANDEDNESS: single
      (D) TOPOLOGY: linear (xi) SEQUENCE DESCRIPTION: SEQ ID NO: 2:

```
GGATCCTTTT TGTTTAACTT TAAGAAGGAG ATATACATAT GCGTCCGTCT ATCCACCGTA      60

CCGCTATCGC TGCTGTTCTG GCTACCGCTT TCGTTGCTGG TACCGCTCTG GCATTCCCGA     120
```

-continued

```
CCATCCCGCT GTCTCGTCTG TTCGACAACG CTATGCTGCG TGCTCACCGT CTGCACCAGC    180

TGGCTTTCGA CACCTACCAG GAATGGGAAG AAGCTTACAT CCCGAAAGAA CAGAAATACT    240

CTTTCCTGCA GAACCCGCAG ACCTCTCTGT GCTTCTCTGA ATCTATCCCG ACCCCGTCTA    300

ACCGTGAAGA AACCCAGCAG AAATCTAACC TGGAACTGCT GCGTATCTCT CTGCTGCTGA    360

TCCAGTCTTG GCTGGAACCG GTTCAGTTCC TGCGTTCTGT TTGGGCTAAC TCTCTGGTTT    420

ACGGTGCTTC TGACTCTAAC GTTTACGACC TGCTGAAAGA CCTGGAAGAA GGTATCCAGA    480

CCCTGATGGG TCGTCTGGAA GACGGTTCTC CGCGTACCGG TCAGATCTTC AAACAGACCT    540

ACTCTAAATT CGACACCAAC TCTCACAACG ACGACGCTCT GCTGAAAAAC TACGGTCTGC    600

TGTACTGCTT CCGTAAAGAC ATGGACAAAG TTGAAACCTT CCTGCGTATC GTTCAGTGCC    660

GTTCTGTTGA AGGTTCTTGC GGTTTCTAAC TCGAG    695
```

(2) INFORMATION FOR SEQ ID NO: 3:

(i) SEQUENCE CHARACTERISTICS:
        (A) LENGTH: 191 amino acids
        (B) TYPE: amino acid
        (C) STRANDEDNESS: single
        (D) TOPOLOGY: linear (xi) SEQUENCE DESCRIPTION: SEQ ID NO: 3:

```
Phe Pro Thr Ile Pro Leu Ser Arg Leu Phe Asp Asn Ala Met Leu Ar
1               5                   10                  15

Ala His Arg Leu His Gln Leu Ala Phe Asp Thr Tyr Gln Glu Trp Gl
            20                  25                  30

Glu Ala Tyr Ile Pro Lys Glu Gln Lys Tyr Ser Phe Leu Gln Asn Pr
            35                  40                  45

Gln Thr Ser Leu Cys Phe Ser Glu Ser Ile Pro Thr Pro Ser Asn Ar
    50                  55                  60

Glu Glu Thr Gln Gln Lys Ser Asn Leu Glu Leu Leu Arg Ile Ser Le
65                  70                  75                  80

Leu Leu Ile Gln Ser Trp Leu Glu Pro Val Gln Phe Leu Arg Ser Va
                85                  90                  95

Trp Ala Asn Ser Leu Val Tyr Gly Ala Ser Asp Ser Asn Val Tyr As
            100                 105                 110

Leu Leu Lys Asp Leu Glu Glu Gly Ile Gln Thr Leu Met Gly Arg Le
            115                 120                 125

Glu Asp Gly Ser Pro Arg Thr Gly Gln Ile Pro Lys Gln Thr Tyr Se
        130                 135                 140

Lys Phe Asp Thr Asn Ser His Asn Asp Asp Ala Leu Leu Lys Asn Ty
145                 150                 155                 160

Gly Leu Leu Tyr Cys Phe Arg Lys Asp Met Asp Lys Val Glu Thr Ph
                165                 170                 175

Leu Arg Ile Val Gln Cys Arg Ser Val Glu Gly Ser Cys Gly Phe
            180                 185                 190
```

(2) INFORMATION FOR SEQ ID NO: 4:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO: 4:

Cys Gly Asn Leu Ser Thr Cys Met Leu Gly Thr Tyr Thr Gln Asp Ph

```
                1               5              10              15

Asn Lys Phe His Thr Phe Pro Gln Thr Ala Ile Gly Val Gly Ala Pr
                            20              25              30
```

(2) INFORMATION FOR SEQ ID NO: 5:

(i) SEQUENCE CHARACTERISTICS:
        (A) LENGTH: 44 amino acids
        (B) TYPE: amino acid
        (C) STRANDEDNESS: single
        (D) TOPOLOGY: linear (xi) SEQUENCE DESCRIPTION: SEQ ID NO: 5:

```
Tyr Ala Asp Ala Ile Phe Thr Asn Ser Tyr Arg Lys Val Leu Gly Gl
1               5              10              15

Leu Ser Ala Arg Lys Leu Leu Gln Asp Ile Met Ser Arg Gln Gln Gl
                20              25              30

Glu Ser Asn Gln Glu Arg Gly Ala Arg Arg Leu
                35              40
```

(2) INFORMATION FOR SEQ ID NO: 6:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO: 6:

```
Gly Ile Val Glu Gln Cys Cys Thr Ser Ile Cys Ser Leu Tyr Gln Le
1               5              10              15

Glu Asn Tyr Cys Asn
                20
```

(2) INFORMATION FOR SEQ ID NO: 7:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 7:

```
Phe Val Asn Gln His Leu Cys Gly Ser His Leu Val Glu Ala Leu Ty
1               5              10              15

Leu Val Cys Gly Glu Arg Gly Phe Phe Tyr Thr Pro Lys Thr
                20              25              30
```

(2) INFORMATION FOR SEQ ID NO: 8:

(i) SEQUENCE CHARACTERISTICS:
        (A) LENGTH: 165 amino acids
        (B) TYPE: amino acid
        (C) STRANDEDNESS: single
        (D) TOPOLOGY: linear (xi) SEQUENCE DESCRIPTION: SEQ ID NO: 8:

```
Ala Pro Pro Arg Leu Ile Cys Asp Ser Arg Val Leu Gln Arg Tyr Le
1               5              10              15

Leu Glu Ala Lys Glu Ala Glu Asn Ile Thr Thr Gly Cys Ala Glu Hi
                20              25              30

Cys Ser Leu Asn Glu Asn Ile Thr Val Pro Asp Thr Lys Val Asn Ph
                35              40              45
```

```
Tyr Ala Trp Lys Arg Met Glu Val Gly Gln Gln Ala Val Glu Val Tr
    50                  55                  60
Gln Gly Leu Ala Leu Leu Ser Glu Ala Val Leu Arg Gly Gln Ala Le
65                  70                  75                  80
Leu Val Asn Ser Ser Gln Pro Trp Glu Pro Leu Gln Leu His Val As
                85                  90                  95
Lys Ala Val Ser Gly Leu Arg Ser Leu Thr Thr Leu Leu Arg Ala Le
                100                 105                 110
Gly Ala Gln Lys Glu Ala Ile Ser Pro Pro Asp Ala Ala Ser Ala Al
                115                 120                 125
Pro Leu Arg Thr Ile Thr Ala Asp Thr Phe Arg Lys Leu Phe Arg Va
            130                 135                 140
Tyr Ser Asn Phe Leu Arg Gly Lys Leu Lys Leu Tyr Thr Gly Glu Al
145                 150                 155                 160
Cys Arg Thr Gly Asp
                165

(2) INFORMATION FOR SEQ ID NO: 9:

(i) SEQUENCE CHARACTERISTICS:
        (A) LENGTH: 133 amino acids
        (B) TYPE: amino acid
        (C) STRANDEDNESS: single
        (D) TOPOLOGY: linear (xi) SEQUENCE DESCRIPTION: SEQ ID NO: 9:

Ala Pro Thr Ser Ser Thr Lys Lys Thr Gln Leu Gln Leu Glu Hi
1               5                   10                  15
Leu Leu Leu Asp Leu Gln Met Ile Leu Asn Gly Ile Asn Asn Tyr Ly
                20                  25                  30
Asn Pro Lys Leu Thr Arg Met Leu Thr Phe Lys Phe Tyr Met Pro Ly
            35                  40                  45
Lys Ala Thr Glu Leu Lys His Leu Gln Cys Leu Glu Glu Glu Leu Ly
50                  55                  60
Pro Leu Glu Glu Val Leu Asn Leu Ala Gln Ser Lys Asn Phe His Le
65                  70                  75                  80
Arg Pro Arg Asp Leu Ile Ser Asn Ile Asn Val Ile Val Leu Glu Le
                85                  90                  95
Lys Gly Ser Glu Thr Thr Phe Met Cys Glu Tyr Ala Asp Glu Thr Al
                100                 105                 110
Thr Ile Val Glu Phe Leu Asn Arg Trp Ile Thr Phe Cys Gln Ser Il
            115                 120                 125
Ile Ser Thr Leu Thr
    130
```